(12) United States Patent
Clark et al.

(10) Patent No.: US 7,868,218 B2
(45) Date of Patent: Jan. 11, 2011

(54) ALKYLAROMATICS PRODUCTION

(75) Inventors: Michael C. Clark, Pasadena, TX (US); Brian Maerz, Chelmsford, MA (US)

(73) Assignees: ExxonMobil Chemical Patents Inc., Houston, TX (US); Badger Licensing, LLC, Cambridge, MA (US)

( * ) Notice: Subject to any disclaimer, the term of this patent is extended or adjusted under 35 U.S.C. 154(b) by 0 days.

(21) Appl. No.: 12/797,115

(22) Filed: Jun. 9, 2010

(65) Prior Publication Data

US 2010/0249472 A1    Sep. 30, 2010

Related U.S. Application Data

(63) Continuation of application No. 12/361,344, filed on Jan. 28, 2009, now Pat. No. 7,772,448, which is a continuation of application No. 11/431,677, filed on May 10, 2006, now Pat. No. 7,501,547.

(51) Int. Cl.
C07C 2/66    (2006.01)
(52) U.S. Cl. ...................................... 585/449; 585/467
(58) Field of Classification Search ................ 585/449, 585/467
See application file for complete search history.

(56) References Cited

U.S. PATENT DOCUMENTS

| | | |
|---|---|---|
| 3,293,192 A | 12/1966 | Maher et al. |
| 3,308,069 A | 3/1967 | Wadlinger et al. |
| 3,442,795 A | 5/1969 | Kerr et al. |
| 3,449,070 A | 6/1969 | McDaniel et al. |
| 3,494,971 A | 2/1970 | Fenske |
| 3,524,820 A | 8/1970 | Hemming |
| 3,631,122 A | 12/1971 | Berger |
| 3,702,886 A | 11/1972 | Argauer et al. |
| 3,709,979 A | 1/1973 | Chu |
| 3,751,504 A | 8/1973 | Keown et al. |
| 3,751,506 A | 8/1973 | Burress |
| 3,755,483 A | 8/1973 | Burress |
| 3,766,093 A | 10/1973 | Chu |
| 3,832,449 A | 8/1974 | Rosinski et al. |
| RE28,341 E | 2/1975 | Wadlinger et al. |
| 3,894,104 A | 7/1975 | Chang et al. |
| 3,923,636 A | 12/1975 | Mead et al. |
| 3,972,983 A | 8/1976 | Ciric |
| 4,016,218 A | 4/1977 | Haag et al. |
| 4,016,245 A | 4/1977 | Plank et al. |
| 4,076,842 A | 2/1978 | Plank et al. |
| 4,107,224 A | 8/1978 | Dwyer |
| RE29,948 E | 3/1979 | Dwyer et al. |
| 4,234,231 A | 11/1980 | Yan |
| 4,401,556 A | 8/1983 | Bezman et al. |
| 4,439,409 A | 3/1984 | Puppe et al. |
| 4,556,477 A | 12/1985 | Dwyer |
| 4,891,458 A | 1/1990 | Innes et al. |
| 4,992,606 A | 2/1991 | Kushnerick et al. |
| 5,073,653 A | 12/1991 | Butler |
| 5,077,445 A | 12/1991 | Le |
| 5,149,894 A | 9/1992 | Holtermann et al. |
| 5,236,575 A | 8/1993 | Bennett et al. |
| 5,250,277 A | 10/1993 | Kresge et al. |
| 5,258,565 A | 11/1993 | Kresge et al. |
| 5,292,698 A | 3/1994 | Chu et al. |
| 5,300,722 A | 4/1994 | Steigelmann et al. |
| 5,334,795 A | 8/1994 | Chu et al. |
| 5,362,697 A | 11/1994 | Fung et al. |
| 5,371,310 A | 12/1994 | Bennett et al. |
| 5,430,211 A | 7/1995 | Pogue et al. |
| 5,453,554 A | 9/1995 | Cheng et al. |
| 5,476,978 A | 12/1995 | Smith, Jr. et al. |
| 5,491,277 A | 2/1996 | Stine et al. |
| 5,493,065 A | 2/1996 | Cheng et al. |
| 5,557,024 A | 9/1996 | Cheng et al. |
| 5,600,048 A | 2/1997 | Cheng et al. |
| 5,856,607 A | 1/1999 | Kim |
| 5,880,320 A | 3/1999 | Netzer |
| 5,998,687 A | 12/1999 | Woodle et al. |
| 6,077,498 A | 6/2000 | Diaz Cabanas et al. |
| 6,231,751 B1 | 5/2001 | Canos et al. |

(Continued)

FOREIGN PATENT DOCUMENTS

CN    1 051 166    12/1990

(Continued)

*Primary Examiner*—Thuan Dinh Dang
(74) *Attorney, Agent, or Firm*—Darryl M. Tyus (57) ABSTRACT

A process is described for producing an alkylaromatic compound in a multistage reaction system comprising at least first and second series-connected alkylation reaction zones each containing an alkylation catalyst. A first feed comprising an alkylatable aromatic compound and a second feed comprising an alkene and one or more alkanes are introduced into said first alkylation reaction zone, having operating conditions, e.g., temperature and pressure, which are controlled effective to cause the alkylatable aromatic compound to be partly in the vapor phase and partly in the liquid phase with the ratio of liquid volume to vapor volume of the feed in each zone to be from about 0.5 to about 10. The aromatic compound and the alkene are reacted in the presence of the alkylation catalyst to form an effluent comprising the alkylaromatic compound, unreacted alkylatable aromatic compound, any unreacted alkene and the alkane, which is withdrawn and then supplied to the second alkylation reaction zone without removal of the alkane.

20 Claims, 4 Drawing Sheets

U.S. PATENT DOCUMENTS

| | | | |
|---|---|---|---|
| 6,252,126 | B1 | 6/2001 | Netzer |
| 6,995,295 | B2 | 2/2006 | Clark et al. |
| 2002/0128529 | A1 | 9/2002 | Chen |
| 2004/0059167 | A1 | 3/2004 | Clark et al. |
| 2004/0171899 | A1 | 9/2004 | Pohl |

FOREIGN PATENT DOCUMENTS

| | | |
|---|---|---|
| EP | 0 323 663 | 4/1992 |
| EP | 0 293 032 | 7/1993 |
| EP | 0 629 549 | 12/1994 |
| EP | 0 432 814 | 9/1995 |
| EP | 0 467 007 | 4/1996 |
| EP | 0 949 227 | 10/1999 |
| EP | 0 485 683 | 1/2001 |
| FR | 2 706 888 | 12/1994 |
| WO | WO 97/17290 | 5/1997 |
| WO | WO 98/07673 | 2/1998 |
| WO | WO 99/65601 | 12/1999 |
| WO | WO 00/39253 | 7/2000 |
| WO | WO 01/21562 | 3/2001 |
| WO | WO 03/044125 | 5/2003 |
| WO | WO 2006/107470 | 10/2006 |
| WO | WO 2006/107471 | 10/2006 |

ALKYLAROMATICS PRODUCTION

CROSS-REFERENCE TO RELATED APPLICATIONS

This application claims priority as a continuation of U.S. Ser. No. 12/361,344, filed Jan. 28, 2009, now U.S. Pat. No. 7,772,448, which is a continuation of U.S. Ser. No. 11/431,677, filed May 10, 2006, now U.S. Pat. No. 7,501,547, the entire contents of which are hereby incorporated by reference herein.

FIELD OF THE INVENTION

The present invention relates to a process for producing alkylaromatic compounds, particularly ethylbenzene.

BACKGROUND OF THE INVENTION

Ethylbenzene is a key raw material in the production of styrene and is produced by the reaction of ethylene and benzene in the presence of an acid catalyst. Older ethylbenzene production plants, typically built before 1980, used $AlCl_3$ or $BF_3$ as the acidic catalyst. Newer plants have in general been switching to zeolite-based acidic catalysts.

Commercial ethylbenzene manufacturing processes typically require the use of polymer grade ethylene, which has a purity exceeding 99.9 mol. %. However, the purification of ethylene streams to polymer grade is a costly process and hence there is considerable interest in developing processes that may operate with lower grade ethylene streams. One such ethylene source is the dilute ethylene obtained as an off gas from the fluid catalytic cracking or steam cracking unit of a petroleum refinery which, after removal of reactive impurities, such as propylene, typically contains about 20-80 wt. % ethylene, with the remainder being ethane together with minor amounts of hydrogen, methane and benzene. Another such dilute ethylene source is the feed stream to an ethylene/ethane distillation splitter.

Three types of ethylation reactor systems are used for producing ethylbenzene, namely, vapor phase reactor systems, liquid phase reactor systems, and mixed phase reactor systems.

In vapor-phase reactor systems, the ethylation reaction of benzene and ethylene is carried out at a temperature in the range of about 380-420° C. and a pressure in the range of 9-15 $kg/cm^2$-g in multiple fixed beds of zeolite catalyst. Ethylene exothermically reacts with benzene to form ethylbenzene, although undesirable chain and side reactions also occur. About 15% of the ethylbenzene formed further reacts with ethylene to form di-ethylbenzene isomers (DEB), tri-ethylbenzene isomers (TEB) and other heavier aromatic products. All these chain reaction products are commonly referred to as polyethylated benzenes (PEBs). In addition to the ethylation reactions, the formation of xylene isomers as trace products occurs by side reactions. This xylene formation in vapor phase processes may yield an ethylbenzene product with about 0.05-0.20 wt. % of xylenes. These xylenes may appear as an impurity in the subsequent styrene product, and are generally considered undesirable.

In order to minimize the formation of PEBs, a stoichiometric excess of benzene, about 400-900% per pass, is applied, depending on process optimization. The effluent from the ethylation reactor contains about 70-85 wt. % of unreacted benzene, about 12-20 wt. % of ethylbenzene product and about 3-4 wt. % of PEBs. To avoid a yield loss, the PEBs are converted back to ethylbenzene by transalkylation with additional benzene, normally in a separate transalkylation reactor.

By way of example, vapor phase ethylation of benzene over the crystalline aluminosilicate zeolite ZSM-5 is disclosed in U.S. Pat. Nos. 3,751,504 (Keown et al.), 3,751,506 (Burress), and 3,755,483 (Burress).

In most cases, vapor phase ethylation systems use polymer grade ethylene feeds. Commercial vapor phase processes employing dilute ethylene feeds have been built and are currently in operation, however the investment costs associated with these processes are high and the products produced contain high concentrations of xylene impurities.

In recent years, the trend in the industry has been to shift away from vapor phase reactors to liquid phase reactors. Liquid phase reactors operate at a temperature in the range of about 180-270° C., which is under the critical temperature of benzene (about 290° C.). One advantage of the liquid phase reactor is the very low formation of xylenes and other undesirable byproducts. The rate of the liquid phase ethylation reaction is normally lower than the vapor phase reaction and higher catalyst volumes are required. However, the lower design temperature of the liquid phase reaction usually economically compensates for the negatives associated with the higher catalyst volume. Due to the lower liquid phase ethylation temperatures, the rate of the side reactions forming PEBs is considerably lower; namely, about 5-8% of the ethylbenzene is converted to PEBs in liquid phase reactions versus the 15-20% converted in vapor phase reactions. Hence the stoichiometric excess of benzene in liquid phase systems is typically 150-400%, compared with 400-900% in vapor phase systems.

Liquid phase ethylation of benzene using zeolite Beta as the catalyst is disclosed in U.S. Pat. No. 4,891,458 and European Patent Publication Nos. 0432814 and 0629549. More recently it has been disclosed that MCM-22 and its structural analogues have utility in alkylation and/or transalkylation reactions; see, for example, U.S. Pat. No. 4,992,606 (MCM-22), U.S. Pat. No. 5,258,565 (MCM-36), U.S. Pat. No. 5,371,310 (MCM-49), U.S. Pat. No. 5,453,554 (MCM-56), U.S. Pat. No. 5,149,894 (SSZ-25); U.S. Pat. No. 6,077,498 (ITQ-1); and U.S. Pat. No. 6,231,751 (ITQ-2).

Commercial liquid phase ethylbenzene plants normally employ polymer grade ethylene. Moreover, although plants may be designed to accept ethylene streams containing up to 30 mol. % ethane by increasing the operating pressure, the additional costs associated with the design, construction and operation of these plants are significant.

Technology has also been developed for the production of ethylbenzene in a mixed phase using reactive distillation. Such a process is described in U.S. Pat. No. 5,476,978. Mixed phase processes may be used with dilute ethylene streams since the reaction temperature of the ethylation reactor is below the dew point of the dilute ethylene/benzene mixture, but well above the bubble point. The diluents of the ethylene feed, which are typically ethane, methane and hydrogen, remain essentially in the vapor phase. The benzene in the reactor is split between vapor phase and liquid phase, and the ethylbenzene and PEB reaction products remain essentially in the liquid phase. However, reactive distillation units are complex and expensive and the catalyst is prone to deactivation as a result of the production of ethylene oligomers.

U.S. Pat. No. 6,252,126 discloses a mixed phase process for producing ethylbenzene by reaction of a dilute ethylene stream containing 3 to 50 mol. % ethylene with a benzene stream containing 75 to 100 wt. % benzene at a temperature at least 10° C. below the boiling point of benzene at the pressure at which the reaction is maintained. The reaction is conducted in an isothermal ethylation section of a reactor vessel that also includes a benzene stripping section, where the unreacted benzene is thermally stripped from the ethylation products. Integrated, countercurrent vapor and liquid traffic is maintained between the ethylation section and the benzene stripping section.

U.S. Pat. No. 6,995,295 describes a mixed phase process for producing ethylbenzene from a combined ethylene/ethane feed using a multistage reaction system comprising a plurality of series-connected alkylation reaction zones each containing an alkylation catalyst. The process employs interstage separation of ethane and/or other diluents from the unreacted feed to increase the ratio of the volume of liquid to the volume of vapor and hence the ethylene conversion in the downstream alkylation reaction zones. There is, however, interest in developing mixed phase alkylation processes in which the capital and operating costs are reduced by, for example, the omission of ancillary equipment for effecting interstage removal of diluents and/or impurities in the feed.

Although the preceding discussion has focused on the production of ethylbenzene, it will be appreciated that similar comments apply to the production of other alkylaromatic compounds, such as cumene and sec-butylbenzene, in which the alkylating group comprises other lower ($C_2$-$C_5$) alkenes, such as propylene and 1-butene and/or 2-butene. In particular, there is interest in developing processes for producing cumene from dilute propylene streams and for producing sec-butylbenzene from dilute $C_4$ olefin streams in which one or more alkylation stages are operated with the benzene being split between the liquid and vapor phase.

According to one embodiment of the present invention it has now been found that, in an aromatics alkylation process using a dilute alkene feed, by controlling the process operating conditions within each reaction zone for alkylation or transalkylation such that the ratio of the volume of liquid to the volume of vapor of feed is in the range of about 0.1 to about 10, the alkene conversion in said zones may be maximized and byproduct production minimized without the need for interstage separation of alkane from the unreacted feed. It has also been found that, whereas most alkylation catalysts or transalkylation catalyst are less active at the lower temperatures required for liquid phase alkylation, MCM-22 and its structural analogues are more active in the liquid phase than in the vapor phase, thereby allowing conversion to be optimized in a mixed phase alkylation or transalkylation reactor system operating at high ratios of the volume of liquid to the volume of vapor.

SUMMARY OF THE INVENTION

In one aspect, the present invention resides in a process for producing an alkylaromatic compound in a multistage reaction system comprising at least first and second series-connected reaction zones each containing an alkylation catalyst and having operating conditions, the process comprising:

(a) introducing a first feed comprising an alkylatable aromatic compound and a second feed comprising an alkene and one or more alkanes into said first reaction zone to form a first feedstock;

(b) controlling said operating conditions of said first reaction zone effective to cause (i) part of said alkylatable aromatic compound to be in the vapor phase and part of said alkylatable aromatic compound to be in the liquid phase; and (ii) the ratio of the volume of liquid to the volume of vapor of said first feedstock in said first reaction zone to be from about 0.1 to about 10;

(c) alkylating said alkylatable aromatic compound with said alkene in the presence of said alkylation catalyst to form a first effluent;

(d) withdrawing said first effluent from said first reaction zone, said first effluent comprising said alkylaromatic compound, unreacted alkylatable aromatic compound, any unreacted alkene and said alkane; and (e) without removing said alkane from said first effluent, supplying a second feedstock comprising said effluent and said alkene to the second reaction zone; and (f) controlling said operating conditions of said second reaction zone effective to cause (i) part of said alkylatable aromatic compound to be in the vapor phase and part of said alkylatable aromatic compound to be in the liquid phase; and (ii) the ratio of the volume of liquid to the volume of vapor of said first feedstock in said first reaction zone to be from about 0.1 to about 10;

(g) alkylating said alkylatable aromatic compound with said alkene in the presence of said alkylation catalyst to form a second effluent comprising additional alkylaromatic compound, unreacted alkylatable aromatic compound, polyalkylated aromatic compound, any unreacted alkene and said alkane.

Preferably, the operating conditions in (b) and (f) are such that the ratio of the volume of liquid to the volume of vapor in each of said first and second reaction zones is from about 0.2 to about 5, such as from about 0.4 to about 2, for example from about 0.5 to about 1.

Typically, the second feed comprises at least 20 wt. % of said alkene, such as from about 20 to 80 wt. % or from about 60 to 80 wt. % of said alkene. Typically, the or each alkane in said second feed has the same number, or less, carbon atoms as said alkene.

In one embodiment, said alkylatable aromatic compound comprises benzene, said second feed comprises ethylene and said alkylaromatic compound comprises ethylbenzene. Conveniently, said operating conditions include a temperature of about 120 to about 270° C. and a pressure of about 675 to about 8300 kPa.

In another embodiment, said alkylatable aromatic compound comprises benzene, said second feed comprises propylene and said alkylaromatic compound comprises cumene. Conveniently, said operating conditions include a temperature of about 80 to about 180° C. and a pressure of about 675 to about 4000 kPa.

In yet another embodiment, said alkylatable aromatic compound comprises benzene and said second feed comprises 1-butene and/or 2-butene. Conveniently, said operating conditions include a temperature of about 50 to about 250° C. and a pressure of about 445 to about 3550 kPa.

Conveniently, said alkylation catalysts comprise a molecular sieve having a Constraint Index of about 2 to about 12 or a Constraint Index of less than about 2.

Conveniently, said molecular sieve having a Constraint Index of about 2 to about 12 comprises a molecular sieve selected from the group consisting of ZSM-5, ZSM-11, ZSM-12, ZSM-22, ZSM-23, ZSM-35, ZSM-48, and mixtures thereof.

Conveniently, said molecular sieve having a Constraint Index of less than about 2 comprises mordenite, TEA-mordenite, zeolite Beta, faujasite, zeolite Y, Ultrastable Y (USY), Dealuminized Y (Deal Y) ZSM-3, ZSM-4, ZSM-5, ZSM-18, ZSM-20, and mixtures thereof.

Conveniently, said alkylation catalyst is selected from the group consisting of MCM-22, PSH-3, SSZ-25, ERB-1, ITQ-1, ITQ-2, MCM-36, MCM-49, MCM-56.

In another aspect, the invention resides in a process for producing ethylbenzene from a feed comprising benzene, ethylene and ethane in a multistage reaction system, said reaction system comprising at least first and second series-connected alkylation reaction zones each containing an alkylation catalyst and having operating conditions, and at least one transalkylation reaction zone comprising a transalkylation catalyst, the process comprising the steps of:

(a) controlling said operating conditions of said first alkylation reaction zone effective to cause (i) part of said benzene of said feed to be in the vapor phase and part of said benzene of said feed to be in the liquid phase, and (ii) the ratio of the volume of liquid to the volume of vapor in said first reaction zone is from about 0.1 to about 10;

(b) reacting said benzene and said ethylene of said feed in the presence of said alkylation catalyst to form a first effluent, said first effluent comprising said ethylbenzene, unreacted benzene, any unreacted ethylene, polyethylbenzene, and said ethane;

(c) withdrawing said first effluent from said first alkylation reaction zone and without removing said ethane from said first effluent, supplying said first effluent to said second alkylation reaction zone;

(d) controlling said operating conditions of said second alkylation reaction zone effective to cause (i) part of said benzene of said first effluent to be in the vapor phase and part of said benzene of said first effluent to be in the liquid phase, and (ii) the ratio of the volume of vapor in said second reaction zone is from about 0.1 to about 10;

(e) reacting said benzene and said ethylene of said first effluent in the presence of said alkylation catalyst to form a second effluent comprising additional ethylbenzene, unreacted benzene, any unreacted ethylene, polyethylbenzene, and said ethane;

(f) separating said polyethylbenzene from said second effluent, and (g) contacting at least portion of said polyethylbenzene with additional benzene in the presence of a transalkylation catalyst under transalkylating conditions in said transalkylation zone, to form additional ethylbenzene, said transalkylation catalyst comprises a molecular sieve selected from the group consisting of MCM-22, PSH-3, SSZ-25, ERB-1, ITQ-1, ITQ-2, MCM-36, MCM-49, MCM-56, zeolite Beta, faujacite, zeolite Y, Ultrastable Y (USY), Dealuminized Y (Deal Y), mordenite, TEA-mordenite, ZSM-3, ZSM-4, ZSM-5, ZSM-18, and ZSM-20, and mixtures thereof.

In another aspect, the invention resides in a process for producing cumene from a feed comprising benzene, propylene and propane in a multistage reaction system, said reaction system comprising at least first and second series-connected alkylation reaction zones each containing an alkylation catalyst and having operating conditions, and at least one transalkylation reaction zone comprising a transalkylation catalyst, the process comprising the steps of:

(a) controlling said operating conditions of said first alkylation reaction zone effective to cause (i) part of said benzene to be in the vapor phase and part of said benzene to be in the liquid phase, and (ii) the ratio of the volume of liquid to the volume of vapor in said first reaction zone is from about 0.1 to about 10;

(b) reacting said benzene and said propylene of said feed in the presence of said alkylation catalyst to form a first effluent, said first effluent comprising said cumene, unreacted benzene, any unreacted propylene, polyisopropylbenzene, and said propane;

(c) withdrawing said first effluent from said first alkylation reaction zone and without removing said propane from said first effluent, supplying said first effluent to said second alkylation reaction zone;

(d) controlling said operating conditions of said second alkylation reaction zone effective to cause (i) part of said benzene to be in the vapor phase and part of said benzene to be in the liquid phase, and (ii) the ratio of the volume of vapor in said second reaction zone is from about 0.1 to about 10;

(e) reacting said benzene and said propylene of said first effluent in the presence of said alkylation catalyst to form a second effluent;

(f) separating said polyisopropylbenzene from said second effluent, and (g) contacting at least portion of said polyisopropylbenzene with additional benzene in the presence of a transalkylation catalyst under transalkylating conditions in said transalkylation zone, to form additional cumene, said transalkylation catalyst comprises a molecular sieve selected from the group consisting of MCM-22, PSH-3, SSZ-25, ERB-1, ITQ-1, ITQ-2, MCM-36, MCM-49, MCM-56, zeolite Beta, faujacite, zeolite Y, Ultrastable Y (USY), Dealuminized Y (Deal Y), mordenite, TEA-mordenite, ZSM-3, ZSM-4, ZSM-5, ZSM-18, and ZSM-20, and mixtures thereof.

In another aspect, the invention resides in a process for producing sec-butylbenzene from a feed comprising benzene, 1-butene or 2-butene and butane in a multistage reaction system, said reaction system comprising at least first and second series-connected alkylation reaction zones each containing an alkylation catalyst and having operating conditions, and at least one transalkylation reaction zone comprising a transalkylation catalyst, the process comprising the steps of:

(a) controlling said operating conditions of said first alkylation reaction zone effective to cause (i) part of said benzene of said feed to be in the vapor phase and part of said benzene of said feed to be in the liquid phase, and (ii) the ratio of the volume of liquid to the volume of vapor in said first reaction zone is from about 0.1 to about 10;

(b) reacting said benzene and said 1-butene or 2-butene of said feed in the presence of said alkylation catalyst to form a first effluent, said first effluent comprising said sec-butylbenzene, unreacted benzene, any unreacted 1-butene or 2-butene, polybutylbenzene, and said butane;

(c) withdrawing said first effluent from said first alkylation reaction zone and without removing said butane from said first effluent, supplying said first effluent and said 1-butene or 2-butene to said second alkylation reaction zone; and (d) controlling said operating conditions of said second alkylation reaction zone effective to cause (i) part of said benzene of said first effluent to be in the vapor phase and part of said benzene of said first effluent to be in the liquid phase, and (ii) the ratio of the volume of liquid to the volume of vapor in said second reaction zone is from about 0.1 to about 10;

(e) reacting said benzene and said 1-butene or 2-butene of said first effluent in the presence of said alkylation catalyst to form a second effluent comprising additional sec-butylbenzene, unreacted benzene, and any unreacted 1-butene or 2-butene, polybutylbenzene, and said propane;

(f) separating said polybutylbenzene from said second effluent of said second alkylation reaction zone, and (g) contacting at least portion of said polybutylbenzene with additional benzene in the presence of a transalkylation catalyst under transalkylating conditions in said transalkylation reaction zone, to form additional sec-butylbenzene, said transalkylation catalyst comprises a molecular sieve selected from the group consisting of MCM-22, PSH-3, SSZ-25, ERB-1, ITQ-1, ITQ-2, MCM-36, MCM-49, MCM-56, zeolite Beta, faujacite, zeolite Y, Ultrastable Y (USY), Dealuminized Y (Deal Y), mordenite, TEA-mordenite, ZSM-3, ZSM-4, ZSM-5, ZSM-18, and ZSM-20, and mixtures thereof.

DETAILED DESCRIPTION OF THE EMBODIMENTS

The present invention provides a mixed phase process for producing alkylaromatic compounds from a dilute alkene feedstock, in which the feedstock also includes an alkane and typically other impurities. Although the process is particularly directed to the production of ethylbenzene from dilute ethylene, it is equally applicable to the production of other $C_2$-$C_6$ alkylaromatic compounds, such as cumene and sec-butylbenzene, as well as $C_6$+alkylaromatics, such as $C_8$-$C_{16}$ linear alkylbenzenes. Where the feedstock is dilute ethylene, the impurities present will normally include ethane, methane and/or hydrogen.

The process involves reacting an alkylatable aromatic compound with the dilute alkene feedstock in a multistage reaction system comprising at least first and second, and normally at least three, series-connected alkylation reaction zones, which each contain an alkylation catalyst and which are typically located in a single reaction vessel. Each alkylation reaction zone is operated under conditions effective not only to cause alkylation of the aromatic compound with the alkene in the presence of the alkylation catalyst, but also to result in the aromatic compound being partly in the vapor phase and partly in the liquid phase. More particularly, as will be discussed in more detail below, the operating conditions in each reaction zone are controlled such that the ratio of the volume of liquid to the volume of vapor in each reaction zone is from about 0.1 to about 10, for example from about 0.2 to about 5, such as from about 0.4 to about 2, for example from about 0.5 to about 1. In determining the liquid to vapor volume ratio in a given reaction zone, the total volume of all the reactants in the liquid phase in the reaction zone (for example, liquid benzene and any dissolved ethylene and/or ethane) is divided by the total volume of all the reactants in the vapor phase in the reaction zone (for example, ethylene, ethane and vapor-phase benzene).

The effluent from each alkylation reaction zone comprises the desired alkylaromatic compound, unreacted alkylatable aromatic compound, any unreacted alkene (overall alkene conversion is expected to be 98-99.99%) and the alkane impurity. Each alkylation reaction zone effluent, except for that from the final alkylation reaction zone, is then passed to the subsequent alkylation reaction zone where additional dilute alkene feedstock is added for reaction with the unreacted aromatic compound. However, unlike the process described in U.S. Pat. No. 6,995,295, the effluent from each alkylation reaction zone is passed directly to the subsequent reaction zone without prior removal of the alkane or other diluents from the effluent thereby eliminating the need for some costly equipment.

In addition to, and upstream of, the series-connected alkylation reaction zones, the reaction system may also include a by-passable reactive guard bed, which is normally located in a pre-reactor separate from the remainder of the alkylation reaction zone, but is part of the reaction system. The reactive guard bed is also loaded with alkylation catalyst, which may be the same or different from the catalyst used in the series-connected, multi-stage reaction system, and is maintained under ambient or up to alkylation conditions. The alkylatable aromatic compound and at least a portion of the dilute alkene feedstock are passed through the reactive guard bed prior to entry into the first zone of the series-connected alkylation reaction zones. The reactive guard bed not only serves to effect the desired alkylation reaction but is also used to remove any reactive impurities in the feeds, such as nitrogen compounds, which could otherwise poison the remainder of the alkylation catalyst. The catalyst in the guard bed is therefore subject to more frequent regeneration and/or replacement than the remainder of the alkylation catalyst and hence the guard bed is normally provided with a by-pass circuit so that the alkylation feedstocks may be fed directly to the series-connected alkylation reaction zones when the guard bed is out of service. The reactive guard bed may operate in all liquid phase or mixed phase in co-current upflow or downflow operation.

The series-connected, multi-stage reaction system used in the process of the invention is normally operated so as to achieve essentially complete conversion of the alkene in the dilute alkene feedstock. However, for some applications, it may be desirable to operate at below 100% alkene conversion and employ a separate finishing reactor downstream of the series-connected, multi-stage reaction system. The finishing reactor would also contain alkylation catalyst, which could be the same or different from the catalyst used in the series-connected, multi-stage reaction system and could be operated under vapor phase, liquid phase or mixed phase alkylation conditions.

In one embodiment of the invention, the series-connected, multi-stage reaction system used in the process of the invention is highly selective to the desired monoalkylated product, such as ethylbenzene, but normally produces at least some polyalkylated species, such as diethylbenzene. Thus the effluent from the final alkylation stage comprises the desired monoalkylated product and the polyalkylated species along with unreacted alkene (if any), unreacted alkylated aromatic compound and the alkane. This effluent is passed to separation scheme in which the alkane, unreacted alkene, unreacted alkylated aromatic compound, and desired monalkylated product are serially separated.

In one embodiment of the invention, the multi-stage reaction system further includes at least one transalkylation zone having a transalkylation catalyst. The remaining polyalkylated species is fed to the transalkylation zone, which may or may not be separate from the alkylation zone, where additional monoalkylated product is produced by reacting the polyalkylated species with additional aromatic compound in the presence of the transalkylation catalyst.

Reactants

The reactants used in the process of the invention include an alkylatable aromatic compound and a dilute alkene alkylating agent.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a heteroatom are also useful provided they do not act as catalyst poisons under the reaction conditions selected.

Substituted aromatic compounds which may be alkylated herein must possess at least one hydrogen atom directly bonded to the aromatic nucleus. The aromatic rings may be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene, with benzene being preferred.

Generally the alkyl groups which may be present as substituents on the aromatic compound contain from about 1 to 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethylto luene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate or cut thereof containing substantial quantities of benzene, toluene and/or xylene constitutes a particularly useful feed for the alkylation process of this invention.

The alkylating agent useful in the process of this invention includes a dilute alkene feed which contains at least one alkane and typically at least one alkane having the same number of carbon atoms as the alkene. For example, where the alkene is ethylene, the alkane may be ethane. Typically, the dilute alkene feed comprises at least 20 wt. % of the alkene, such as from about 20 to about 80 wt. %, for example from about 60 to about 80 wt. % of the alkene. It is recognized that feed sources may undergo purification (for example by distillation) prior to being fed to the alkylation catalyst. One particularly useful feed is the dilute ethylene stream obtained as an off gas from the fluid catalytic cracking unit of a petroleum refinery.

Preferably, the reactants in the process of the invention are benzene and dilute ethylene and the desired reaction product is ethylbenzene.

Alkylation and Transalkylation Catalysts

In one embodiment of this invention, the alkylation catalysts and transalkylation catalysts used in the process of the invention may comprise one or more molecular sieves selected from the group consisting of MCM-22, PSH-3, SSZ-25, ERB-1, ITQ-1, ITQ-2, MCM-36, MCM-49 and MCM-56.

MCM-22 and its use to catalyze the synthesis of alkylaromatics, including ethylbenzene and cumene, are described in U.S. Pat. Nos. 4,992,606; 5,077,445; and 5,334,795. PSH-3 is described in U.S. Pat. No. 4,439,409. SSZ-25 and its use in aromatics alkylation are described in U.S. Pat. No. 5,149,894. ERB-1 is described in European Patent No. 0293032. ITQ-1 is described in U.S. Pat. No. 6,077,498. ITQ-2 is described in U.S. Pat. No. 6,231,751. MCM-36 is described in U.S. Pat. Nos. 5,250,277 and 5,292,698. U.S. Pat. No. 5,258,565 describes the synthesis of alkylaromatics, including ethylbenzene and cumene, using a catalyst comprising MCM-36. MCM-49 is described in U.S. Pat. No. 5,236,575. The use of MCM-49 to catalyze the synthesis of alkylaromatics, including ethylbenzene and cumene, is described in U.S. Pat. Nos. 5,493,065 and 5,371,310. MCM-56 is described in U.S. Pat. No. 5,362,697. The use of MCM-56 to catalyze the synthesis of alkylaromatics, including ethylbenzene and cumene, is described in U.S. Pat. Nos. 5,557,024 and 5,453,554. The entire contents of all the above patent specifications are incorporated herein by reference.

MCM-22 and the related molecular sieves discussed in the preceding paragraph are preferred since these materials show enhanced alkylation activity and selectivity in the liquid phase as compared with the vapor phase.

In another embodiment of this invention, the alkylation catalysts and transalkylation catalysts may comprise one or more a medium pore molecular sieves having a Constraint Index of 2-12 (as defined in U.S. Pat. No. 4,016,218), including ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. The entire contents of all the above patent specifications are incorporated herein by reference.

In still another embodiment of this invention, the alkylation catalysts and transalkylation catalysts may comprise one or more large pore molecular sieves having a Constraint Index less than 2. Suitable large pore molecular sieves include zeolite Beta, zeolite Y, Ultrastable Y (USY), Dealuminized Y (DealY), mordenite, TEA-mordenite ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (DealY) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

The above molecular sieves may be used as the alkylation catalyst or the transalkylation catalyst in the process of the invention without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 wt. % of the composite.

In any of the embodiments of this invention, the alkylation catalyst or transalkylation catalyst used in one stage of a series-connected, multi-stage alkylation or transalkylation reaction zone may be the same or different from the alkylation catalyst or transalkylation catalyst used in other stage of such alkylation or transalkylation reaction zone. In addition, the alkylation catalysts or transalkylation catalysts used in one or more reaction zones may comprise a single molecular sieve or a mixture of molecular sieves. The same catalyst may be used in reaction zone for transalkylation or the reaction zone for alkylation of the present process. Preferably, however, different catalysts are chosen for the two zones, so as to be tailored for the particular reactions catalyzed therein. For example, in one embodiment, zeolite Beta or MCM-22, either in bound or unbound form, is used in the reactive guard bed; zeolite Beta or MCM-22, MCM-36, MCM-49 or MCM-56 is used in the series-connected, multi-stage alkylation reaction zones; and zeolite Beta, mordenite, TEA-mordenite, ZSM-4, zeolite Y, Ultrastable Y (USY), Dealuminized Y (Deal Y), ZSM-3, or ZSM-4 is used in the transalkylation zone. Alternatively, MCM-22, MCM-36, MCM-49 or MCM-56 may also be used in the transalkylation zone. In such an embodiment, any finishing reactor could include MCM-22 for liquid phase operation or ZSM-5 for vapor phase operation.

Reaction Conditions

In the process of the invention, the alkylation reaction in each of the series-connected alkylation reaction zones takes place under mixed liquid and vapor phase conditions which may be maintained throughout such zones, such that the alkylatable aromatic compound is partly in the vapor phase and partly in the liquid phase. Moreover, the operating conditions in each alkylation reaction zone are controlled so that the ratio of the volume of liquid to the volume of vapor in each reaction zone is from about 0.1 to about 10, for example from about 0.2 to about 5, such as from about 0.4 to about 2.0, for example from about 0.5 to about 1. By maintaining the ratio of the volume of liquid to the volume of vapor at these levels, it is found that the alkene conversion may be maximized without interstage separation of the alkane impurity, especially when the alkylation catalyst is an MCM-22 family molecular sieve.

In this respect, it is to be appreciated that the ratio of the volume of liquid to the volume of vapor in a mixed phase alkylation reactor employing a dilute alkene feed is a function of many variables, including temperature, pressure, dilute alkene feed composition, the weight ratio of aromatics to alkene, and the number of interstage feed injection points (feed distribution among the reaction zones). Each of these variables must be understood and monitored in order to maintain the ratio of the volume of liquid to the volume of vapor at the desired level.

Particular conditions for carrying out the mixed phase alkylation of benzene with ethylene to produce ethylbenzene may include a temperature of from about 150 to about 270° C., a pressure of about 675 to about 8300 kPa; such as a temperature from about 170 to 220° C. and pressure of about 1500 to 4000 kPa, a WHSV based on ethylene of from about 0.1 to about 10 $hr^{-1}$, and a mole ratio of benzene to ethylene from about 1 to about 10.

Particular conditions for carrying out the mixed phase alkylation of benzene with propylene to produce cumene may include a temperature of from about 80 to about 180° C., a pressure of about 675 to about 4000 kPa; such as a temperature from about 100 to 160° C. and pressure of about 1375 to 3000 kPa, a WHSV based on propylene of from about 0.1 to about 10 $hr^{-1}$, and a mole ratio of benzene to propylene from about 1.0 to about 10.0.

Particular conditions for carrying out the mixed phase alkylation of benzene with 1-butene and/or 2-butene to produce sec-butylbenzene may include a temperature of from about 50 to about 250° C., a pressure of about 355 to about 3550 kPa, a WHSV based on butene of from about 0.1 to about 20 $hr^{-1}$, and a mole ratio of benzene to butene from about 1.0 to about 10.0.

Where the alkylation system includes a reactive guard bed, this may be operated under liquid phase conditions or vapor phase conditions or mixed liquid/vapor phase conditions, but is preferably operated under liquid phase conditions. In the case of ethylbenzene production, the guard bed will preferably operate at a temperature between about 20 and about 270° C. and a pressure between about 675 to about 8300 kPa. In the case of cumene production, the guard bed will preferably operate at a temperature from about 25 to 180° C. and pressure from about 675 to 4000 kPa. In the case of sec-butylbenzene production, the guard bed will preferably operate at a temperature from about 50 to 250° C. and pressure from about 445 to 3550 kPa.

The transalkylation reaction may also take place under liquid phase conditions or vapor phase conditions or mixed liquid/vapor phase conditions, but preferably takes place under liquid phase conditions. Particular conditions for carrying out the liquid phase transalkylation of benzene with polyethylbenzenes may include a temperature of from about 150° C. to about 260° C., a pressure of 7000 kPa or less, a WHSV based on the weight of the total liquid feed to the reaction zone of from about 0.5 to about 100 $hr^{-1}$ and a mole ratio of benzene to polyethylbenzene of from about 1.0 to about 30.0. Particular conditions for carrying out the liquid phase transalkylation of benzene with polypropylbenzenes may include a temperature of from about 150° C. to about 300° C., a pressure of 5500 kPa or less, a WHSV based on the weight of the total liquid feed to the reaction zone of from about 0.1 to about 20.0 $hr^{-1}$ and a mole ratio of benzene to polypropylbenzene of from about 1.0 to about 10.0. Particular conditions for carrying out the liquid phase transalkylation of benzene with polybutylbenzenes may include a temperature of 100 to 300° C., a pressure of 1000 to 7000 kPa, a weight hourly space velocity of 1 to 50 $hr^{-1}$ on total feed, and a benzene to polybutylbenzene weight ratio of about 1.0 to about 10.0.

Figure 1:
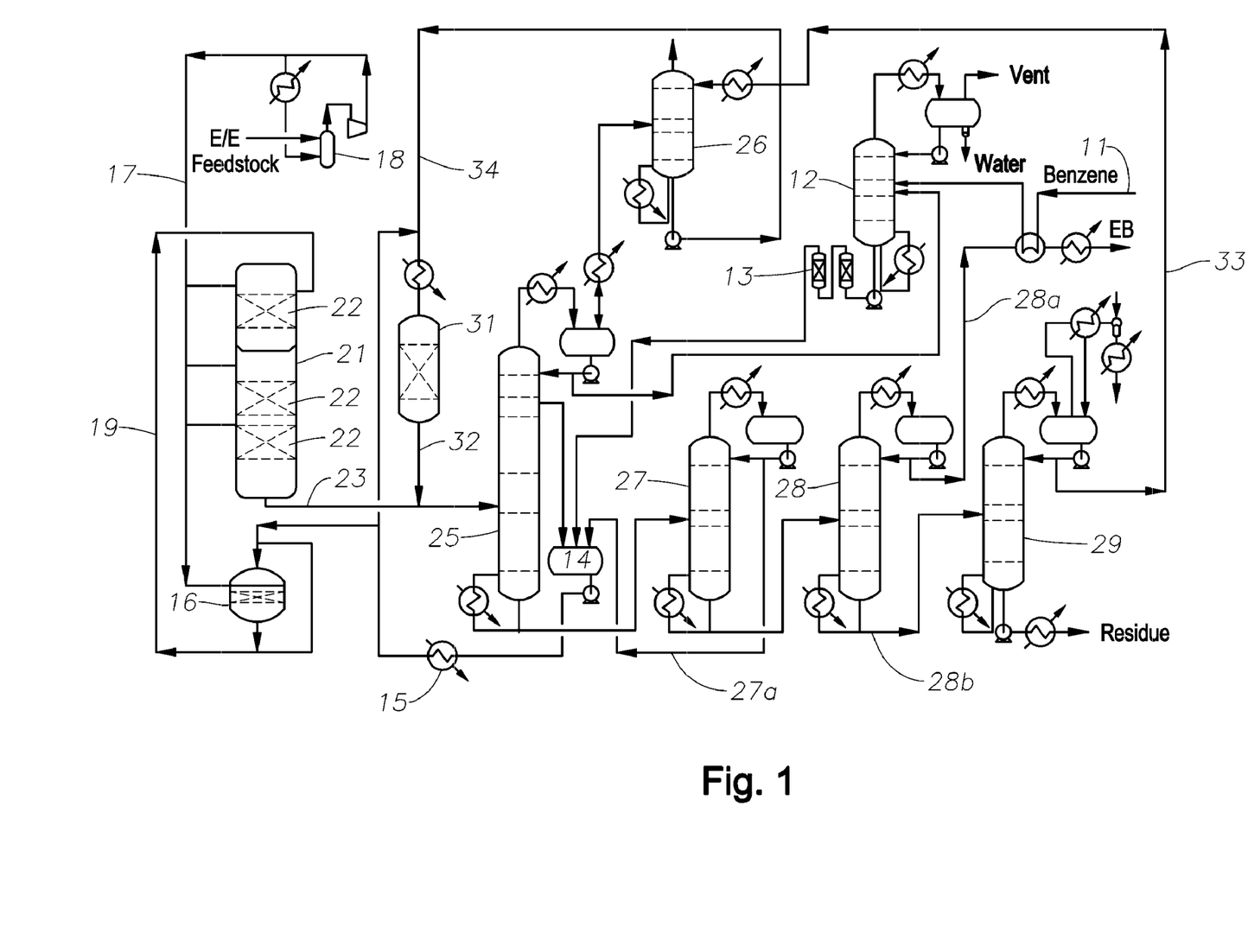
FIG. 1 is a flow diagram of a process for producing ethylbenzene in accordance with one embodiment of the invention.

One embodiment of the process of the invention, in which the alkylatable aromatic compound is benzene and the alkylating agent is a dilute ethylene stream, is shown in FIG. 1.

Referring now to FIG. 1, a benzene feed 11 is passed to a drying column 12, where the water content of the benzene is preferably reduced to below 20 ppm. From the drying column 12, the benzene is passed to a reservoir 14 by way of treaters 13 which serve to remove catalyst poisons, particularly nitrogen and sulfur containing organic species from the benzene. From the reservoir 14, the benzene is pumped to a heat exchanger 15, where the benzene is indirectly heated by high pressure steam, before being fed to a reactive guard bed 16 and transalkylator 31.

The reactive guard bed 16 also receives a dilute ethylene feed 17 from a compressor 18 such that the benzene and dilute ethylene pass cocurrently down through a bed of alkylation catalyst in the reactive guard bed. Alternately, the flow may be co-current upflow. The reactive guard bed 16 typically operates at or near to 100% ethylene conversion but may operate at lower conversions (alternately, no ethylene may be introduced to the reactive guard bed) so that the reactive guard bed effluent 19 leaving the reactive guard bed is composed of ethylbenzenes, unreacted benzene and unreactive light impurities (mainly ethane) from the dilute ethylene feed. The reactive guard bed effluent 19 is then passed to the top bed in a main alkylation reactor 21, which includes a plurality of vertically spaced, series-connected catalyst beds 22. Each catalyst bed 22 also receives the dilute ethylene feed 17 such that the ethylene and the benzene-containing reactive guard bed effluent 19 from the guard bed 16 or the previous bed 22 pass cocurrently down through the catalyst bed 22. Again each catalyst bed 22 of the main alkylation reactor 21 is typically operated at or near to 100% ethylene conversion. Alternately or in addition, the first inlet bed(s) of the main alkylation reactor 21 may operate at less than 100% ethylene conversion while the overall conversion is at or near 100% (for example 97-100%).

The effluent from each catalyst bed 22, except for the bottom catalyst bed, of the main alkylation reactor 21 is passed directly to the next, adjacent bed without any interstage separation of alkanes. The bottom catalyst bed effluent 23, which contains the desired ethylbenzene product as well as unreacted benzene and small quantities of polyethylated benzenes and ethane, is fed initially to a prefractionator 25 where the ethane is removed as overhead and passed to a scrubber 26 where any benzene retained in the ethane is adsorbed by, for example, the polyethylated benzenes produced in the process, such as PEB stream 33. The bottoms fraction from the prefractionator 25 is passed to a benzene column 27 where the unreacted benzene is removed as overhead stream 27a and recycled to the reservoir 14. The bottoms fraction from the benzene tower is passed to an ethylbenzene column 28 where the desired ethylbenzene is recovered as overhead stream 28a and the bottoms fraction stream 28b is passed to a PEB column 29. The polyethylated benzenes, mostly diethylbenzene, are removed in the PEB column 29 and at least a portion of PEB stream 33 is passed through the scrubber 26 before being fed as PEB feed 34 to a transalkylator 31. The transalkylator 31 also receives a supply of benzene from the reservoir 14 and is operated under conditions such that 20-80% of the polyethylated benzenes are converted to ethylbenzene. The effluent 32 from the transalkylator is combined with the effluent 23 from the main alkylation reactor 21 as it passes to the prefractionator 25 and then the benzene column 27, ethylbenzene column 28 and PEB column 29.

The invention will now be more particularly described with reference to the following Example.

EXAMPLE

The alkylation of benzene with a feed comprising 65 mole % ethylene and 35 mole % ethane was tested in an adiabatic pilot plant reactor comprising 4 vertically spaced catalyst beds, each containing 0.45 kg of an MCM-49 catalyst (80 wt. % MCM-49/20 wt. % alumina) and with each of the three lower catalysts beds being located below a 6 inch (15.2 cm) thick layer of sand. Water cooling coils were provided after the second and third catalyst beds.

The ethylene employed was chemical grade ethylene (99.0 wt. % purity) supplied by Air Liquide, whereas the ethane (99.0 wt. % purity) was supplied by Air Liquide. The benzene (99.99+wt. % purity) was obtained directly from the ExxonMobil's Baytown Chemical plant. Each of the feeds to the pilot plant unit was initially passed through a molecular sieve drier to remove water and any basic impurities.

All of the benzene was fed to the uppermost catalyst bed at a rate of 24.762 lb/hr (11.191 kg/hr), whereas the mixed ethylene/ethane feed was supplied to each of the catalysts beds at a rate of 3.059 SCFH, standard cubic feet per hour (0.087 m$^3$/hr) such that the ethylene WHSV was 1 hr$^{-1}$ and the total benzene to ethylene molar ratio over the 4 catalyst beds was 2.9:1. The product from each catalyst bed was cascaded, without interstage ethane removal, to the next adjacent bed.

Figure 2:
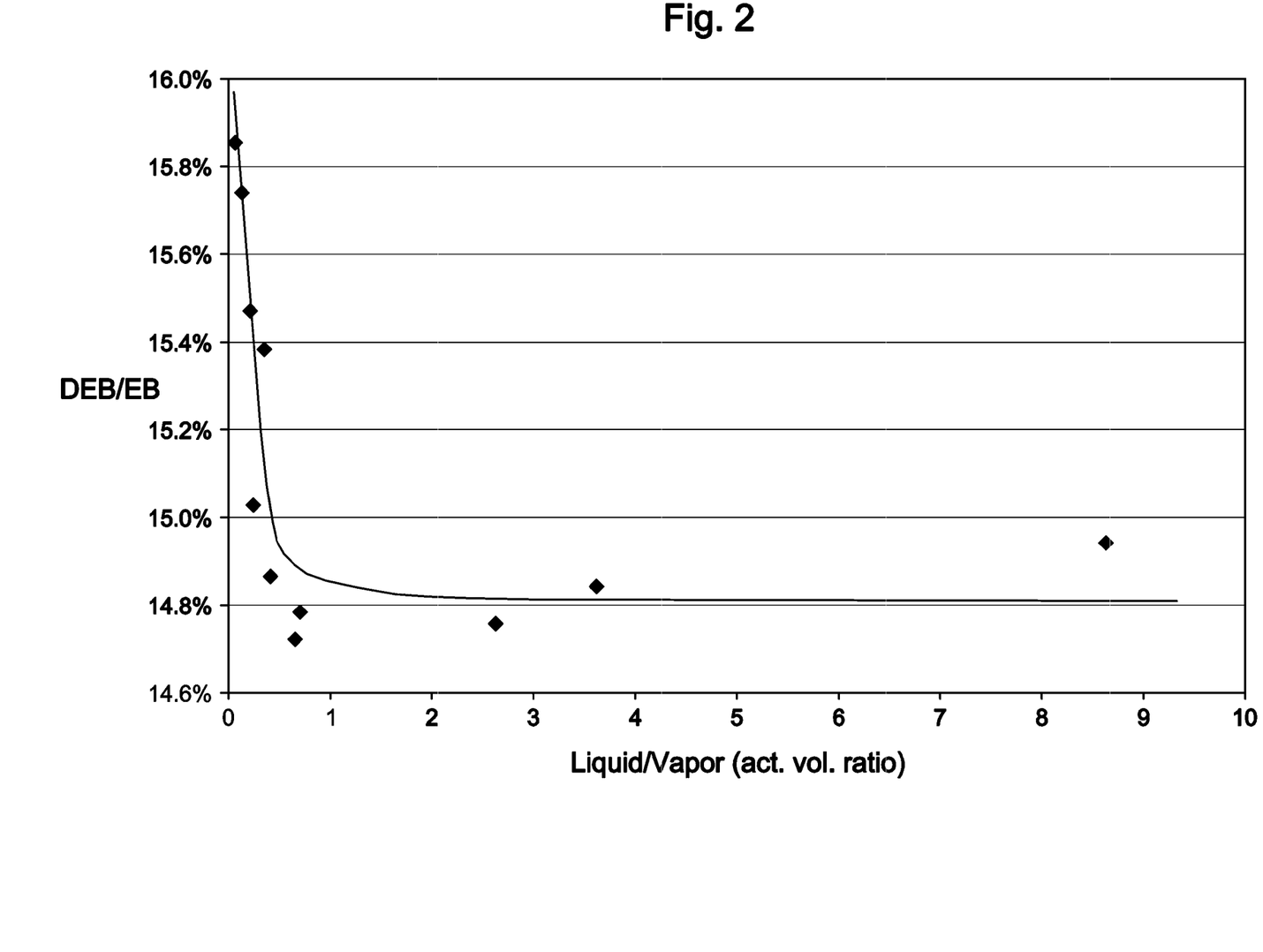
FIGS. 2 to 4 are graphs plotting the diethylbenzene (DEB) to ethylbenzene (EB) product weight ratio against the ratio of the volume of liquid to the volume of vapor for the second, third and fourth catalyst beds respectively in the pilot plant process for alkylating benzene with a mixed feed of ethylene and ethane described in the Example.
Figure 3:
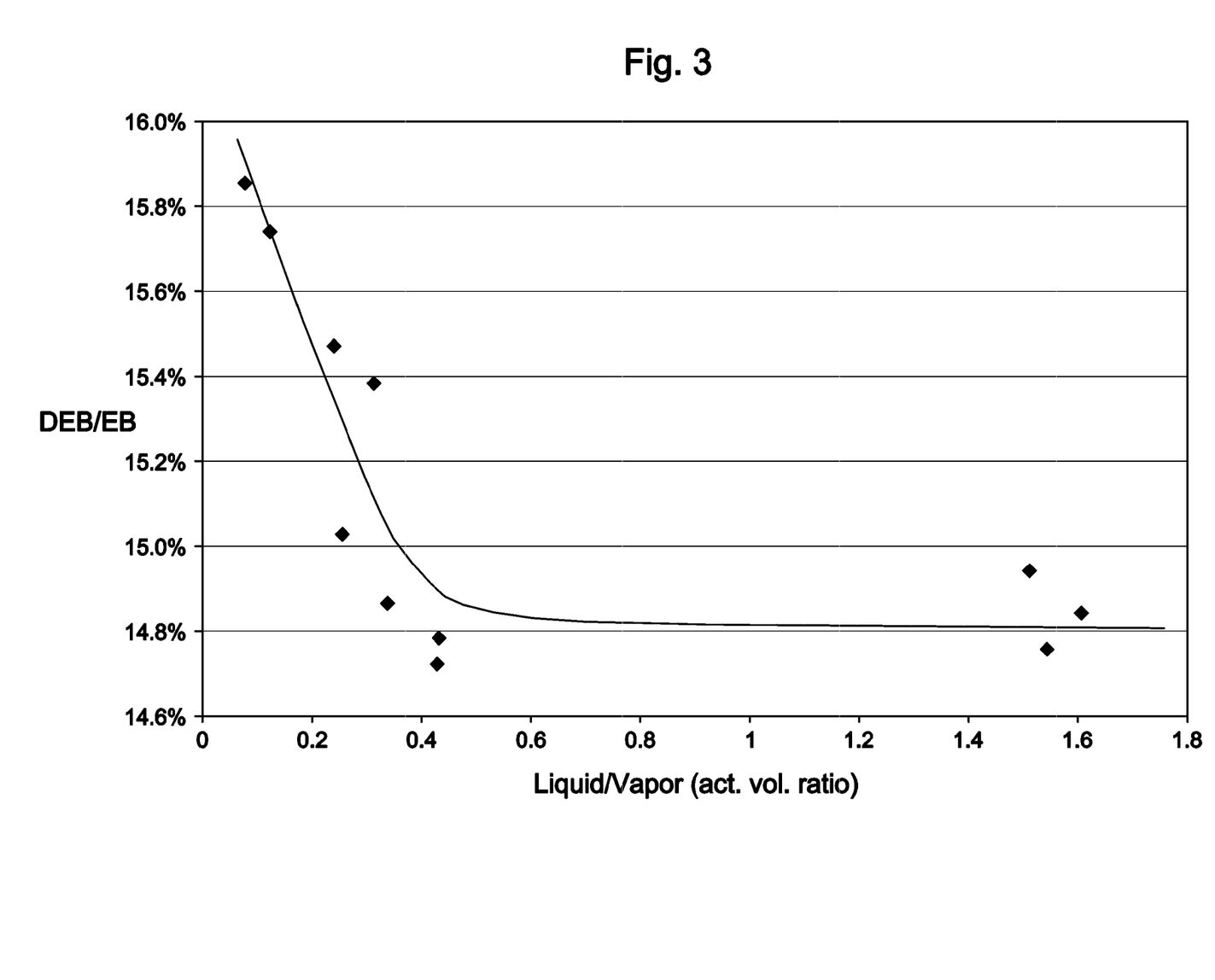
Figure 4:
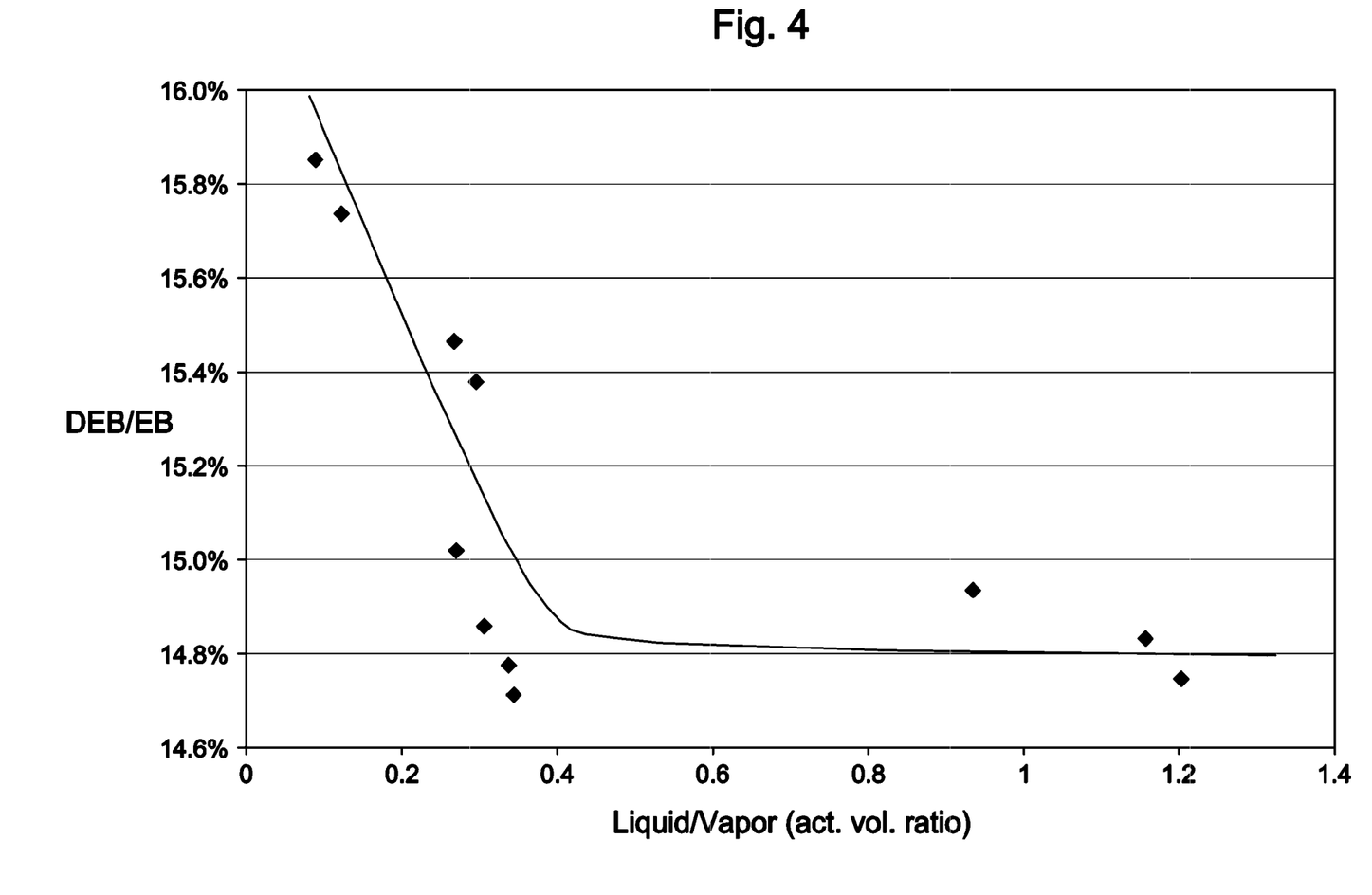

The reactor temperature and pressure were 190° C. and 350 psig (2514 kPa) and the conditions in the reactor were varied to adjust the ratio of the volume of liquid to the volume of vapor in each bed. For example, an increase in temperature or a decrease in pressure causes a decrease in the ratio of the volume of liquid to the volume of vapor. Conversely, an increase in the molar ratio of ethylene to ethane or an increase in the benzene to ethylene molar ratio causes an increase in the ratio of the volume of liquid to the volume of vapor. Samples of the product exiting each catalyst bed were analyzed by gas chromatography and the weight ratio of diethylbenzene (DEB) to ethylbenzene (EB) in each product stream was measured. The results are shown in FIGS. 2 to 4, from which it will be seen that the weight ratio of DEB to EB in the product from each catalyst bed decreases rapidly as the ratio of the volume of liquid to the volume of vapor (as measured at the actual reactor conditions and referred to as act. vol. ratio) in the bed increases above 0.1 but the rate of decrease becomes less pronounced as the ratio of the volume of liquid to the volume of vapor approaches 0.5.

All patents, patent applications, test procedures, priority documents, articles, publications, manuals, and other documents cited herein are fully incorporated by reference for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A process for producing an alkylaromatic compound in a multistage reaction system comprising at least first and second series-connected alkylation reaction zones each containing an alkylation catalyst and having operating conditions, the process comprising the steps of:
   (a) introducing a first feed comprising an alkylatable aromatic compound and a second feed comprising an alkene and one or more alkanes into said first alkylation reaction zone to form a first feedstock;
   (b) controlling said operating conditions of said first alkylation reaction zone by adjusting temperature or pressure effective to cause (i) part of said alkylatable aromatic compound to be in the vapor phase and part of said alkylatable aromatic compound to be in the liquid phase, and (ii) the ratio of the volume of liquid to the volume of vapor of said first feedstock in said first reaction zone to be from about 0.5 to about 10 to maintain a dialkylaromatic/alkylaromatic weight ratio of less than 15%;
   (c) alkylating said alkylatable aromatic compound with said alkene in the presence of said alkylation catalyst to form a first effluent;
   (d) withdrawing said first effluent from said first alkylation reaction zone, said first effluent comprising said alkylaromatic compound, unreacted alkylatable aromatic compound, any unreacted alkene and said alkane;
   (e) without removing said alkane from said first effluent, supplying a second feedstock comprising said first effluent and said alkene to the second alkylation reaction zone;
   (f) controlling said operating conditions of said second alkylation reaction zone by adjusting temperature or pressure effective to cause (i) part of said alkylatable aromatic compound to be in the vapor phase and part of said alkylatable aromatic compound to be in the liquid phase, and (ii) the ratio of the volume of liquid of said second feedstock to the volume of vapor of said second feedstock in said second reaction zone to be from about 0.5 to about 10 to maintain a dialkylaromatic/alkylaromatic weight ratio of less than 15%; and
   (g) alkylating said alkylatable aromatic compound with said alkene in the presence of said alkylation catalyst to form a second effluent comprising additional alkylaromatic compound, unreacted alkylatable aromatic compound, polyalkylated aromatic compound, any unreacted alkene and said alkane, wherein said alkylation catalysts in each of said first and second alkylation reaction zones comprise a molecular sieve independently selected from the group consisting of zeolite Beta, faujacite, zeolite Y, Ultrastable Y (USY), Dealuminized Y (Deal Y), mordenite, TEA-mordenite, ZSM-3, ZSM-4, ZSM-5, ZSM-18, and ZSM-20, and mixtures thereof.

2. The process of claim 1, wherein the operating conditions in steps (b) and (f) are such that the ratio of the volume of liquid to the volume of vapor in each of said first and second reaction zones is from about 0.5 to about 5.

3. The process of claim 1, wherein the operating conditions in steps (b) and (f) are such that the ratio of the volume of liquid to the volume of vapor in each of said first and second reaction zones is from about 0.5 to about 2.

4. The process of claim 1, wherein the operating conditions in steps (b) and (f) are such that the ratio of the volume of liquid to the volume of vapor in each of said first and second reaction zones is from about 0.5 to about 1.

5. The process of claim 1, wherein said second feed comprises at least 20 wt. % of said alkene.

6. The process of claim 1, wherein said second feed comprises about 20 to about 80 wt. % of said alkene.

7. The process of claim 1, wherein said second feed comprises about 60 to about 80 wt. % of said alkene.

8. The process of claim 1, wherein said alkane in said second feed has the same number, or less, carbon atoms as said alkene.

9. The process of claim 1, wherein said alkene comprises ethylene, said alkylatable aromatic compound comprises benzene and said alkylaromatic compound comprises ethylbenzene.

10. The process of claim 9, wherein said operating conditions in step (b), and optionally step (f), include a temperature of about 120 to about 270° C. or a pressure of about 675 to about 8300 kPa.

11. The process of claim 1, wherein said alkene comprises propylene, said alkylatable aromatic compound comprises benzene and said alkylaromatic compound comprises cumene.

12. The process of claim 11, wherein said operating conditions in step (b), and optionally step (f), include a temperature of about 80 to about 180° C. or a pressure of about 675 to about 4000 kPa.

13. The process of claim 1, wherein said alkene comprises 1-butene and/or 2-butene, said alkylatable aromatic compound comprises benzene and said alkylaromatic compound comprises sec-butylbenzene.

14. The process of claim 13, wherein said operating conditions in step (b), and optionally step (f), include a temperature of about 50 to about 250° C. or a pressure of about 355 to about 3550 kPa.

15. The process of claim 1, further comprising the steps of:
   (h) separating said polyalkylated aromatic compounds from said second effluent of said second alkylation reaction zone, and
   (i) contacting at least portion of said polyalkylated aromatic compounds with additional said alkylatable aromatic compound in the presence of a transalkylation catalyst under transalkylating conditions, to form additional monoalkylaromatic compound.

16. The process of claim 1, further comprising the step of contacting said feed with said alkylation catalyst in a by-passable pre-reactor separate from and upstream of said series-connected, multistage reaction system.

17. The process of claim 1, further comprising the step of contacting unreacted alkylatable aromatic compound and unreacted alkene from said multistage reaction system under alkylation conditions with said alkylation catalyst in a finishing reactor separate from and downstream of said multistage reaction system.

18. A process for producing ethylbenzene from a feed comprising benzene, ethylene and ethane in a multistage reaction system, said reaction system comprising at least first and second series-connected alkylation reaction zones each containing an alkylation catalyst and having operating conditions, and at least one transalkylation reaction zone comprising a transalkylation catalyst, the process comprising the steps of:
   (a) controlling said operating conditions of said first alkylation reaction zone by adjusting temperature or pressure effective to cause (i) part of said benzene of said feed to be in the vapor phase and part of said benzene of said feed to be in the liquid phase, and (ii) the ratio of the volume of liquid to the volume of vapor in said first reaction zone is from about 0.5 to about 10 to maintain a diethylbenzene/ethylbenzene weight ratio of less than 15%;

(b) reacting said benzene and said ethylene of said feed in the presence of said alkylation catalyst to form a first effluent, said first effluent comprising said ethylbenzene, unreacted benzene, any unreacted ethylene, polyethylbenzene, and said ethane;

(c) withdrawing said first effluent from said first alkylation reaction zone and without removing said ethane from said first effluent, supplying said first effluent to said second alkylation reaction zone;

(d) controlling said operating conditions of said second alkylation reaction zone by adjusting temperature or pressure effective to cause (i) part of said benzene of said first effluent to be in the vapor phase and part of said benzene of said first effluent to be in the liquid phase, and (ii) the ratio of the volume of vapor in said second reaction zone is from about 0.5 to about 10 to maintain a diethylbenzene/ethylbenzene weight ratio of less than 15%;

(e) reacting said benzene and said ethylene of said first effluent in the presence of said alkylation catalyst to form a second effluent comprising additional ethylbenzene, unreacted benzene, any unreacted ethylene, polyethylbenzene, and said ethane, wherein said alkylation catalysts in each of said first and second alkylation reaction zones comprise a molecular sieve independently selected from the group consisting of zeolite Beta, faujacite, zeolite Y, Ultrastable Y (USY), Dealuminized Y (Deal Y), mordenite, TEA-mordenite, ZSM-3, ZSM-4, ZSM-5, ZSM-18, and ZSM-20, and mixtures thereof;

(f) separating said polyethylbenzene from said second effluent, and (g) contacting at least portion of said polyethylbenzene with additional benzene in the presence of a transalkylation catalyst under transalkylating conditions in said transalkylation zone, to form additional ethylbenzene, said transalkylation catalyst comprises a molecular sieve selected from the group consisting of MCM-22, PSH-3, SSZ-25, ERB-1, ITQ-1, ITQ-2, MCM-36, MCM-49, MCM-56, and mixtures thereof.

19. A process for producing cumene from a feed comprising benzene, propylene and propane in a multistage reaction system, said reaction system comprising at least first and second series-connected alkylation reaction zones each containing an alkylation catalyst and having operating conditions, and at least one transalkylation reaction zone comprising a transalkylation catalyst, the process comprising the steps of:

(a) controlling said operating conditions of said first alkylation reaction zone by adjusting temperature or pressure effective to cause (i) part of said benzene to be in the vapor phase and part of said benzene to be in the liquid phase, and (ii) the ratio of the volume of liquid to the volume of vapor in said first reaction zone is from about 0.5 to about 10 to maintain a di-isopropylbenzene/isopropylbenzene weight ratio of less than 15%;

(b) reacting said benzene and said propylene of said feed in the presence of said alkylation catalyst to form a first effluent, said first effluent comprising said cumene, unreacted benzene, any unreacted propylene, polyisopropylbenzene, and said propane;

(c) withdrawing said first effluent from said first alkylation reaction zone and without removing said propane from said first effluent, supplying said first effluent to said second alkylation reaction zone;

(d) controlling said operating conditions of said second alkylation reaction zone by adjusting temperature or pressure effective to cause (i) part of said benzene to be in the vapor phase and part of said benzene to be in the liquid phase, and (ii) the ratio of the volume of vapor in said second reaction zone is from about 0.5 to about 10 to maintain a di-isopropylbenzene/isopropylbenzene weight ratio of less than 15%;

(e) reacting said benzene and said propylene of said first effluent in the presence of said alkylation catalyst to form a second effluent, wherein said alkylation catalyst in each of said first and second alkylation reaction zones comprise a molecular sieve independently selected from the group consisting of zeolite Beta, faujacite, zeolite Y, Ultrastable Y (USY), Dealuminized Y (Deal Y), mordenite, TEA-mordenite, ZSM-3, ZSM-4, ZSM-5, ZSM-18, and ZSM-20;

(f) separating said polyisopropylbenzene from said second effluent, and (g) contacting at least portion of said polyisopropylbenzene with additional benzene in the presence of a transalkylation catalyst under transalkylating conditions in said transalkylation zone, to form additional cumene, said transalkylation catalyst comprises a molecular sieve selected from the group consisting of MCM-22, PSH-3, SSZ-25, ERB-1, ITQ-1, ITQ-2, MCM-36, MCM-49, MCM-56, and mixtures thereof.

20. A process for producing sec-butylbenzene from a feed comprising benzene, 1-butene or 2-butene and butane in a multistage reaction system, said reaction system comprising at least first and second series-connected alkylation reaction zones each containing an alkylation catalyst and having operating conditions, and at least one transalkylation reaction zone comprising a transalkylation catalyst, the process comprising the steps of:

(a) controlling said operating condition of said first alkylation reaction zone by adjusting temperature or pressure effective to cause (i) part of said benzene of said feed to be in the vapor phase and part of said benzene of said feed to be in the liquid phase, and (ii) the ratio of the volume of liquid to the volume of vapor in said first reaction zone is from about 0.5 to about 10 to maintain a di-sec-butylbenzene/sec-butylbenzene weight ratio of less than 15%;

(b) reacting said benzene and said 1-butene or 2-butene of said feed in the presence of said alkylation catalyst to form a first effluent, said first effluent comprising said sec-butylbenzene, unreacted benzene, any unreacted 1-butene or 2-butene, polybutylbenzene, and said butane;

(c) withdrawing said first effluent from said first alkylation reaction zone and without removing said butane from said first effluent, supplying said first effluent and said 1-butene or 2-butene to said second alkylation reaction zone; and (d) controlling said operating conditions of said second alkylation reaction zone by adjusting temperature or pressure effective to cause (i) part of said benzene of said first effluent to be in the vapor phase and part of said benzene of said first effluent to be in the liquid phase, and (ii) the ratio of the volume of liquid to the volume of vapor in said second reaction zone is from about 0.5 to about 10 to maintain a di-sec-butylbenzene/sec-butylbenzene weight ratio of less than 15%;

(e) reacting said benzene and said 1-butene or 2-butene of said first effluent in the presence of said alkylation catalyst to form a second effluent comprising additional sec-butylbenzene, unreacted benzene, and any unreacted 1-butene or 2-butene, polybutylbenzene, and said propane, wherein said alkylation catalysts in each of said first and second alkylation reaction zones comprise a molecular sieve independently selected from the group consisting of zeolite Beta, faujacite, zeolite Y, Ultrastable Y (USY), Dealuminized Y (Deal Y), mordenite, TEA-mordenite, ZSM-3, ZSM-4, ZSM-5, ZSM-18, and ZSM-20, and mixtures thereof;

(f) separating said polybutylbenzene from said second effluent of said second alkylation reaction zone, and (g) contacting at least portion of said polybutylbenzene with additional benzene in the presence of a transalkylation catalyst under transalkylating conditions in said transalkylation reaction zone, to form additional sec-butylbenzene, said transalkylation catalyst comprises a molecular sieve selected from the group consisting of MCM-22, PSH-3, SSZ-25, ERB-1, ITQ-1, ITQ-2, MCM-36, MCM-49, MCM-56, and mixtures thereof.

* * * * *